(12) United States Patent
Porter

(10) Patent No.: US 6,651,270 B1
(45) Date of Patent: Nov. 25, 2003

(54) CLEANING SYSTEM

(76) Inventor: Keith M. Porter, 9050 Blind Path Rd., Unit #9, St. Pete Beach, FL (US) 33706

( * ) Notice: Subject to any disclaimer, the term of this patent is extended or adjusted under 35 U.S.C. 154(b) by 0 days.

(21) Appl. No.: 09/912,690

(22) Filed: Jul. 26, 2001

(51) Int. Cl.[7] ................................................. A47K 4/00
(52) U.S. Cl. ................................................. 4/662; 4/605
(58) Field of Search ............................ 4/596, 597, 605, 4/662, 903

(56) References Cited

U.S. PATENT DOCUMENTS

| | | | | |
|---|---|---|---|---|
| 4,444,358 A | * | 4/1984 | Spohn et al. | 222/231 X |
| 4,554,690 A | * | 11/1985 | Knapp et al. | 4/596 X |
| 4,563,780 A | * | 1/1986 | Pollack | 4/605 X |
| 4,872,225 A | * | 10/1989 | Wagner | 4/662 |
| 6,463,600 B1 | * | 10/2002 | Conway et al. | 4/662 |
| 6,550,080 B1 | * | 4/2003 | Grewal | 4/662 |

* cited by examiner

*Primary Examiner*—Charles E. Phillips
(74) *Attorney, Agent, or Firm*—Edward P. Dutkiewicz

(57) ABSTRACT

A cleaning system comprises a shower enclosure with a water source. A hollow Y-shaped adaptor member with an input end is provided. The input end is coupled to the water source and a pair of output ends. The first output end is coupled to a shower head. Each output end has an operator controlled on/off valve. A chemical dispensing assembly is provided, having a chemical reservoir and a retention chamber. An operator controlled spring activated check valve is provided. Last provided is a set of hollow dispensing tubes. The tubes are adapted to be coupled to the enclosure. The set of tubes includes an input segment, adapted to couple the water and chemical output line of the dispensing member. The set of tubes includes a plurality of hollow linear segments, each having a plurality of pin hole apertures, a plurality of elbow segments, and an end stopper.

1 Claim, 5 Drawing Sheets

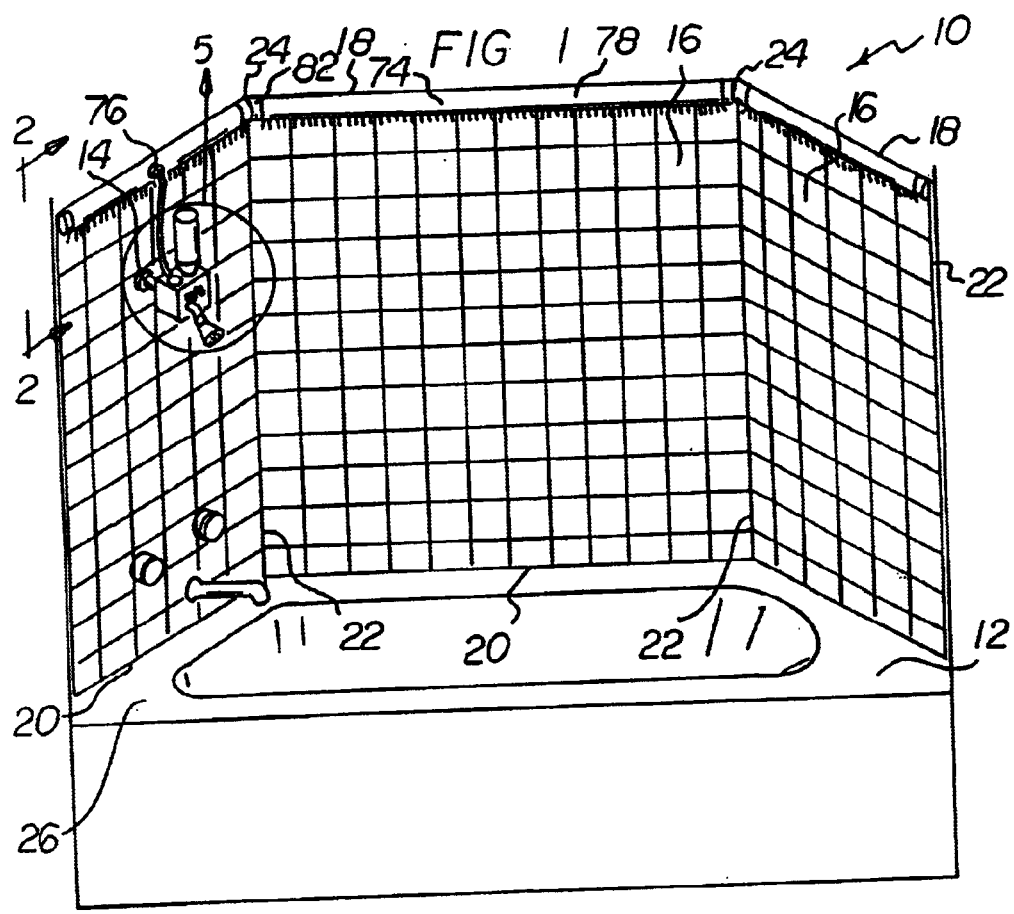
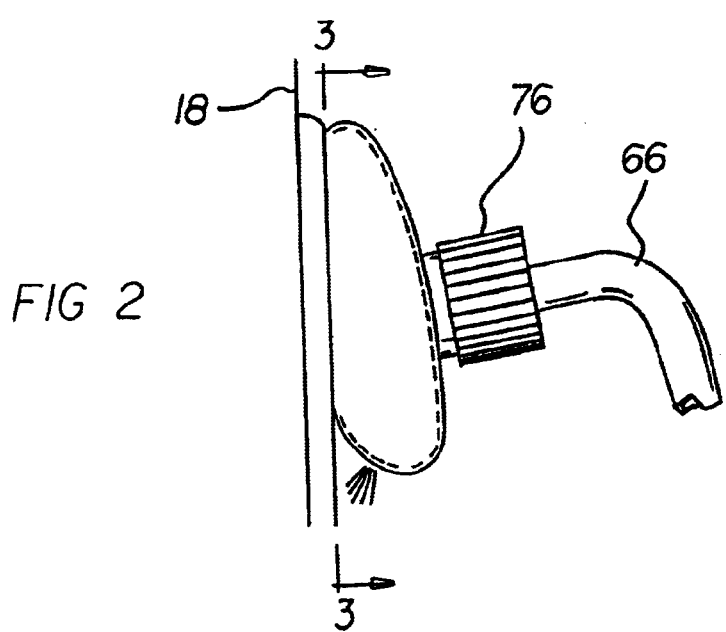

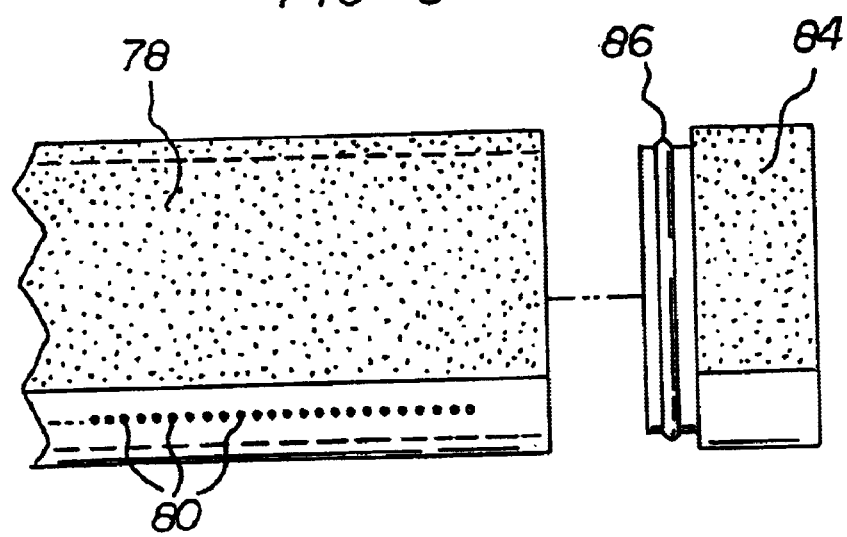
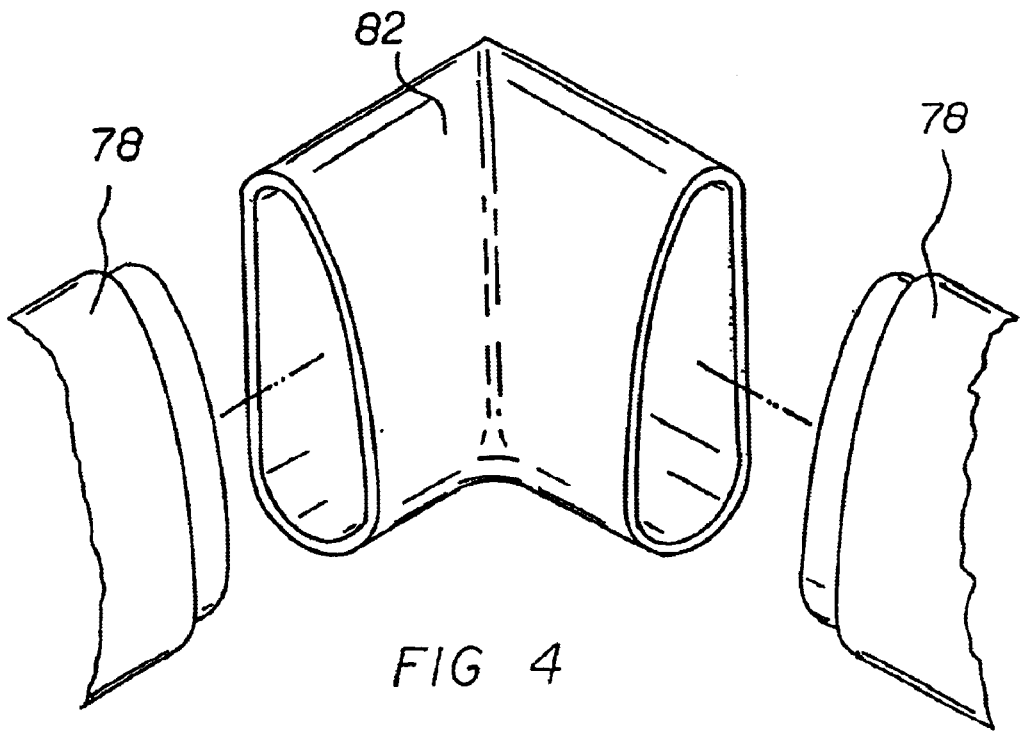

CLEANING SYSTEM

BACKGROUND OF THE INVENTION

1. Field of the Invention

The present invention relates to a cleaning system and more particularly pertains to sanitizing, rinsing and disinfecting a shower enclosure.

2. Description of the Prior Art

The use of cleaning systems of conventional designs and configurations is known in the prior art. More specifically, cleaning systems of conventional designs and configurations previously devised and utilized for the purpose of cleaning through known methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,872,225 to Wagner discloses a cleaning apparatus and method for bathing enclosures and U.S. Pat. No. 4,383,341 to Altman discloses a bathtub self-cleaning system.

While these devices fulfill their respective, particular objectives and requirements, the aforementioned patents do not describe a cleaning system that allows for sanitizing, rinsing and disinfecting a shower enclosure.

In this respect, the cleaning system according to the present invention substantially departs from the conventional concepts and designs of the prior art, and in doing so provides an apparatus primarily developed for the purpose of sanitizing, rinsing and disinfecting a shower enclosure.

Therefore, it can be appreciated that there exists a continuing need for a new and improved cleaning system which can be used for sanitizing, rinsing and disinfecting a shower enclosure. In this regard, the present invention substantially fulfills this need.

SUMMARY OF THE INVENTION

In view of the foregoing disadvantages inherent in the known types of cleaning systems of conventional designs and configurations now present in the prior art, the present invention provides an improved cleaning system. As such, the general purpose of the present invention, which will be described subsequently in greater detail, is to provide a new and improved cleaning system and method which has all the advantages of the prior art and none of the disadvantages.

To attain this, the present invention essentially comprises a shower enclosure. The shower enclosure has an elevated water source. The shower enclosure also has a plurality of contiguous walls. Each of the contiguous walls has an upper edge and a lower edge. The contiguous walls have side edges. The side edges meet at corners. The shower enclosure further has an entrance opening between the walls. Provided next is a hollow Y-shaped adaptor member. The adaptor member has a single input end. The input end is coupled to the water source. The input end is additionally coupled to a pair of output ends. A first output end and a second output end are included in the pair of output ends. The first output end is coupled to a shower head. Each output end has an operator controlled on/off valve. In this manner the water flow to the various outputs is controlled. Further provided is a chemical dispensing assembly. The chemical dispensing assembly has a chemical reservoir. The chemical dispensing assembly also has a retention chamber. An operator controlled spring activated check valve is provided between the chemical reservoir and the retention chamber. The chemical reservoir has a top end. The top end has air holes. The air holes prevent suction within the reservoir. The chemical reservoir also has a bottom end. The bottom end is coupled to the check valve. The retention chamber has a pair of apertures. A first aperture and a second aperture are included in the pair of apertures. The first aperture is coupled to the second output end of the adaptor member. The second aperture is coupled to a water and chemical output line. The retention chamber further has a clasping member. The clasping member is adapted to be coupled to the input end of the adaptor member. When chemical is released into the retention chamber through the check valve and water is released into the retention chamber through the operator controlled on/off valve of the second output end of the adaptor member, the released chemical and released water mix before entering the water and chemical output line. Last provided is a set of hollow dispensing tubes. The hollow dispensing tubes are adapted to be adhesively coupled to the walls adjacent to the upper edge of the shower enclosure. The set of dispensing tubes includes an input segment. The input segment is adapted to couple the water and chemical output line of the chemical dispensing member. The set of dispensing tubes also includes a plurality of hollow linear segments. Each hollow linear segment has a plurality of pin hole apertures. The pin hole apertures are configured to spray water at the walls. The set of dispensing tubes also includes a plurality of right angle elbow segments. The linear segments are coupled to other linear segments. The linear segments are also coupled to the elbow segments for fitting in the corners of the bathing enclosure. The linear portions are terminated with an end stopper. All of the tubes of the set are coupled with snap fitting and with o-rings. The water and chemical mixture flows through the output line of the chemical dispensing assembly and into the dispensing tubes. In this manner the mixture is sprayed on the walls of the bathing enclosure, keeping the walls clean between uses.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved cleaning system which has all of the advantages of the prior art cleaning systems of conventional designs and configurations and none of the disadvantages.

It is another object of the present invention to provide a new and improved cleaning system which may be easily and efficiently manufactured and marketed.

It is further object of the present invention to provide a new and improved cleaning system which is of durable and reliable constructions.

An even further object of the present invention is to provide a new and improved cleaning system which is susceptible of a low cost of manufacture with regard to both materials and labor, and which accordingly is then susceptible of low prices of sale to the consuming public, thereby making such cleaning system economically available to the buying public.

Even still another object of the present invention is to provide a cleaning system for sanitizing, rinsing and disinfecting a shower enclosure.

Lastly, it is an object of the present invention to provide a new and improved cleaning system comprising a shower enclosure with a water source. A hollow Y-shaped adaptor member with an input end is provided. The input end is coupled to the water source and a pair of output ends. The first output end is coupled to a shower head. Each output end has an operator controlled on/off valve. A chemical dispensing assembly is provided, having a chemical reservoir and a retention chamber. An operator controlled spring activated check valve is provided. Last provided is a set of hollow dispensing tubes. The tubes are adapted to be coupled to the enclosure. The set of tubes includes an input segment, adapted to couple the water and chemical output line of the dispensing member. The set of tubes includes a plurality of hollow linear segments, each having a plurality of pin hole apertures, a plurality of elbow segments, and an end stopper.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective illustration of the preferred embodiment of the present invention.

FIG. 2 is an end elevational view of the present invention taken along line 2—2 of FIG. 1.

FIG. 3 is an exploded view of the end stopper of the present invention taken along line 3—3 of FIG. 2.

FIG. 4 is an exploded view of an elbow segment of the present invention.

The same reference numerals refer to the same parts throughout the various Figures.

DESCRIPTION OF THE PREFERRED EMBODIMENT

Figure 5:
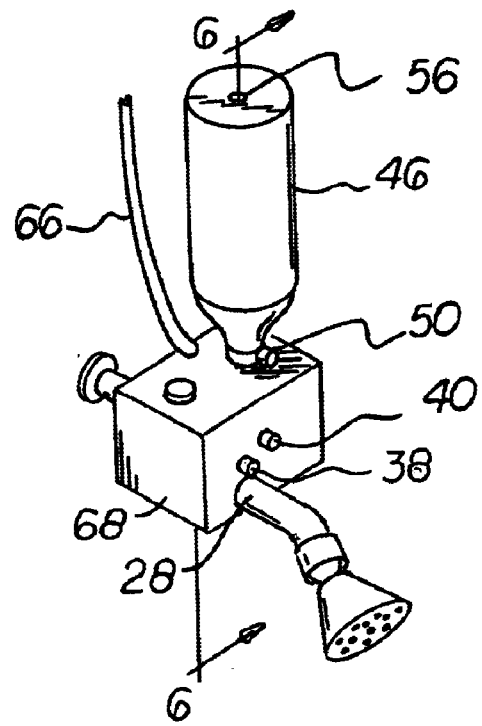
FIG. 5 is perspective illustration of the adaptor member and chemical dispensing assembly associated with the present invention taken at circle 5 of FIG. 1.
Figure 6:
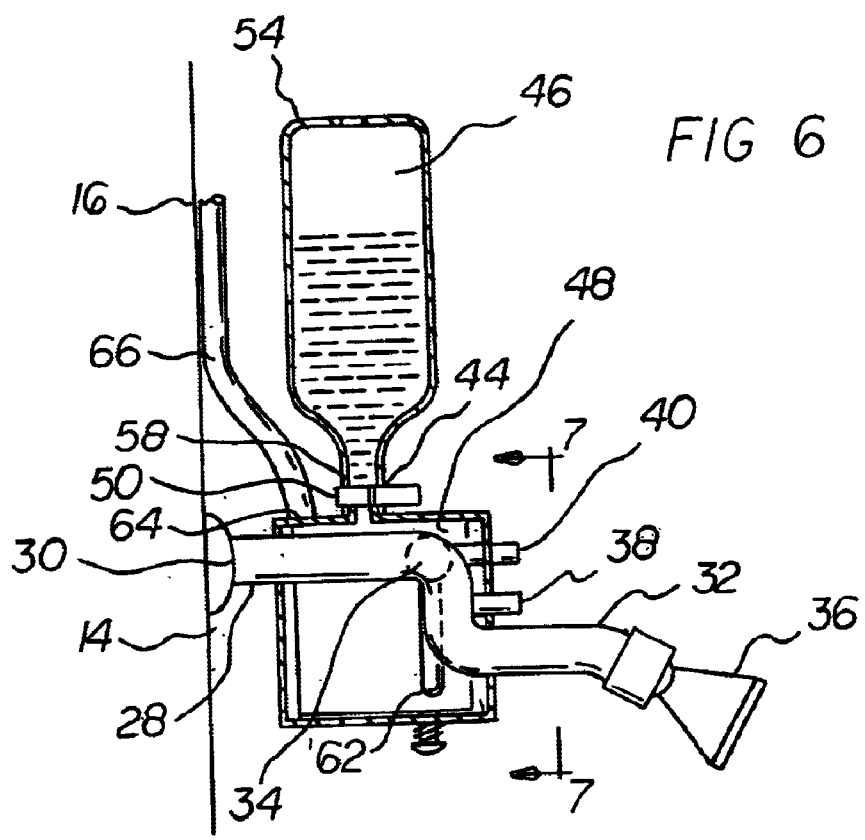
FIG. 6 is a cross-sectional view of the present invention taken along line 6—6 of FIG. 5.
Figure 7:
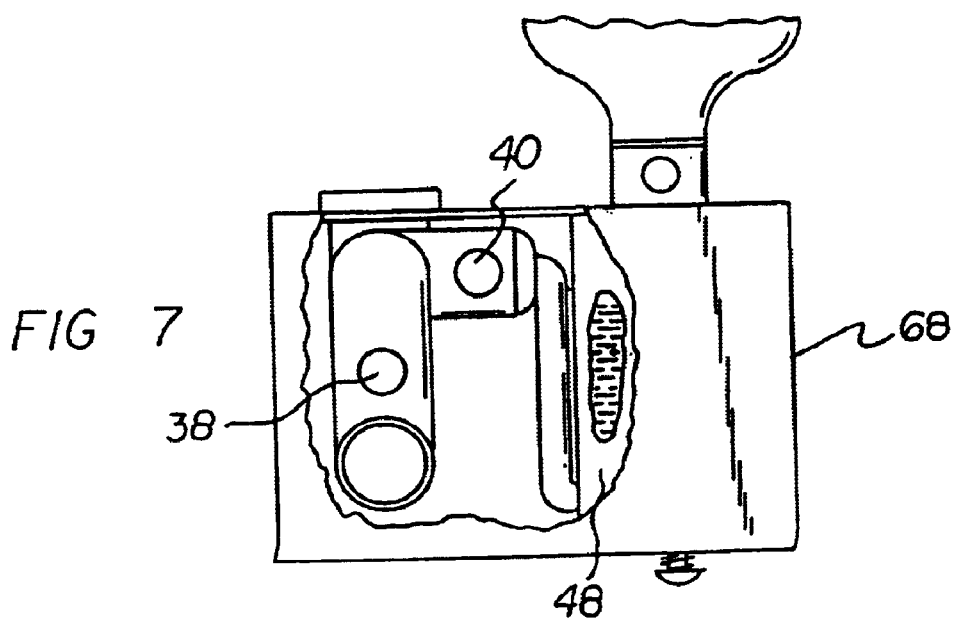
FIG. 7 is a front view of the present invention taken along line 7—7 of FIG. 6.

With reference now to the drawings, and in particular to FIG. 1 thereof, the preferred embodiment of the new and improved cleaning system embodying the principles and concepts of the present invention and generally designated by the reference numeral 10 will be described.

The present invention, the cleaning system 10 is comprised of a plurality of components. Such components in their broadest context include a shower enclosure, a hollow Y-shaped adaptor member, a chemical dispensing assembly, and a set of hollow dispensing tubes. Such components are individually configured and correlated with respect to each other so as to attain the desired objective.

First provided is a shower enclosure 12. The shower enclosure has an elevated water source 14. The shower enclosure also has a plurality of contiguous walls 16. Each of the contiguous walls has an upper edge 18 and a lower edge 20. The contiguous walls have side edges 22. The side edges meet at corners 24. The shower enclosure further has an entrance opening 26 between the walls.

Provided next is a hollow Y-shaped adaptor member 28. The adaptor member has a single input end 30. The input end is coupled to the water source. The input end is additionally coupled to a pair of output ends 32, 34. A first output end 32 and a second output end 34 are included in the pair of output ends. The first output end 32 is coupled to a shower head 36. Each output end has an operator controlled on/off valve 38, 40. In this manner the water flow to the various outputs is controlled.

Further provided is a chemical dispensing assembly 44. The chemical dispensing assembly has a chemical reservoir 46. The chemical dispensing assembly also has a retention chamber 48. An operator controlled spring activated check valve 50 is provided between the chemical reservoir and the retention chamber. The chemical reservoir has a top end 54. The top end has air holes 56. The air holes prevent suction within the reservoir. The chemical reservoir also has a bottom end 58. The bottom end is coupled to the check valve. The retention chamber has a pair of apertures 62, 64. A first aperture 62 and a second aperture 64 are included in the pair of apertures. The first aperture 62 is coupled to the second output end of the adaptor member. The second aperture 64 is coupled to a water and chemical output line 66. The retention chamber further has a clasping member 68. The clasping member is adapted to be coupled to the input end of the adaptor member. When chemical is released into the retention chamber through the check valve and water is released into the retention chamber through the operator controlled on/off valve of the second output end of the adaptor member, the released chemical and released water mix before entering the water and chemical output line.

Last provided is a set of hollow dispensing tubes 74. The hollow dispensing tubes are adapted to be adhesively coupled to the walls adjacent to the upper edge of the shower enclosure. The set of dispensing tubes includes an input segment 76. The input segment is adapted to couple the water and chemical output line of the chemical dispensing member. The set of dispensing tubes also includes a plurality of hollow linear segments 78. Each hollow linear segment has a plurality of pin hole apertures 80. The pin hole apertures are configured to spray water at the walls. The set of dispensing tubes also includes a plurality of right angle elbow segments 82. The linear segments are coupled to other linear segments. The linear segments are also coupled to the elbow segments for fitting in the corners of the bathing enclosure. The linear portions are terminated with an end stopper 84. All of the tubes of the set are coupled with snap fitting and with o-rings 86. The water and chemical mixture flows through the output line of the chemical dispensing assembly and into the dispensing tubes. In this manner the mixture is sprayed on the walls of the bathing enclosure, keeping the walls clean between uses.

Figure 8:
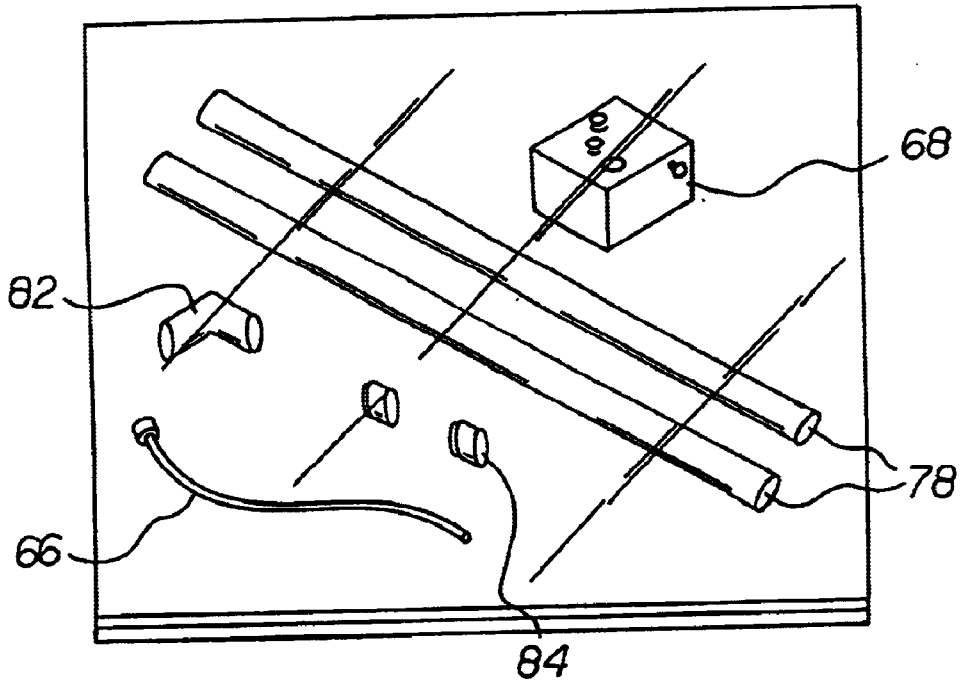
FIG. 8 is perspective illustration of the present invention contained in a blister pack.

The cleaning system is also adapted to be disassembled and packaged in blister pack to ease the transportation and sale of the system as a product as shown in FIG. 8.

Figure 9:
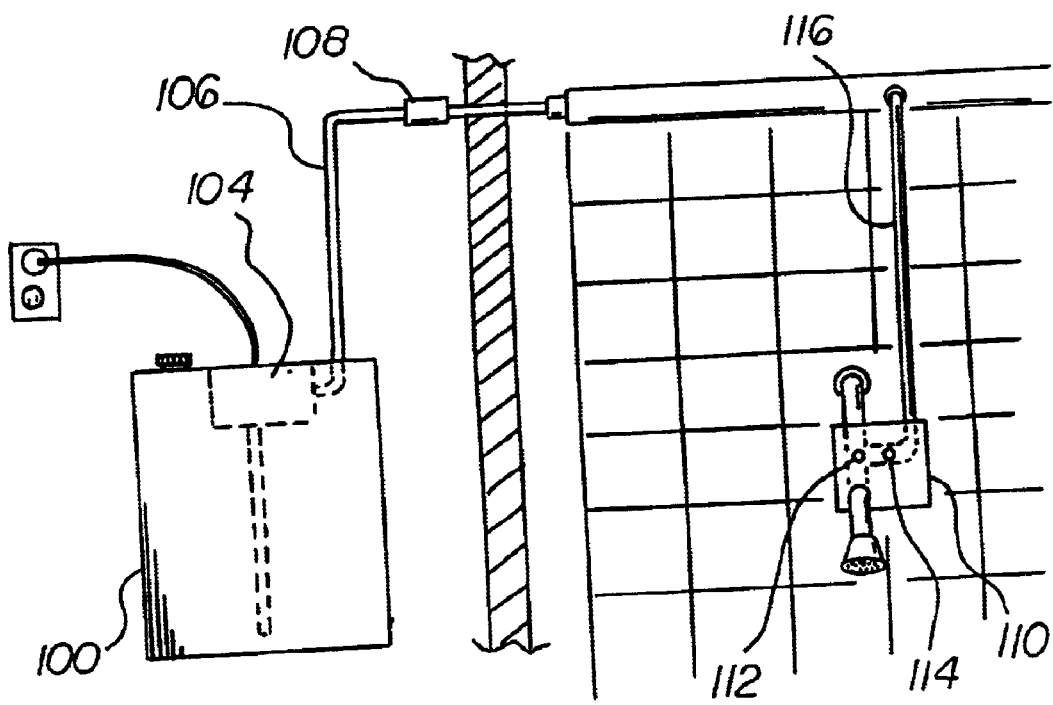
FIG. 9 is a perspective illustration of an alternative embodiment utilized for industrial sites.
Figure 10:
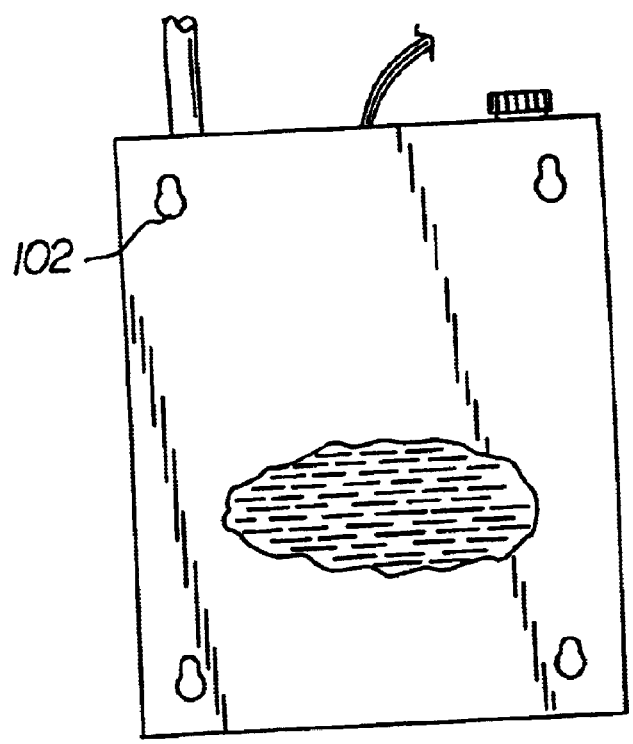
FIG. 10 is rear view of a chemical reservoir of the alternative embodiment of the present invention.

As shown in FIG. 9, the cleaning system of the present invention may be adapted for industrial use. In such a case the chemical reservoir 100 is located at a remote location with respect to the shower enclosure. Such reservoir is of an industrial size to accommodate a larger cleaning surface and/or more frequent usage. The reservoir has a plurality of hooking apertures 102 to couple to a wall as shown in FIG. 10. The reservoir further has a pump 104 to transfer the contents of the reservoir to the shower enclosure upon activation of the system. The cleaning solution is transferred through a first conduit 106. This first conduit is connected to the set of hollow dispensing tubes through a second conduit 116. The system further has a control box 110 located adjacent the water source in the shower enclosure with a shower activation switch 112 and a cleaning switch 114.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A cleaning system adapted for industrial use comprising:

a conventional shower enclosure having an elevated water source and a plurality of contiguous walls each with an upper edge and with side edges meeting at corners;

a hollow Y-shaped adaptor member having a single input end coupled to the water source and a pair of output ends including a first output end coupled to a shower head and a second output end for connection to a hollow dispensing assembly, a control box having a shower activation switch and a cleaning switch, said box being located adjacent the water source in the shower enclosure;

a chemical dispensing assembly having a chemical reservoir being located at a remote location with respect to the shower enclosure and being of an industrial size to accommodate a larger cleaning surface, the reservoir further having a pump therein to transfer the contents of the reservoir to the shower enclosure upon activation of the cleaning switch; and said hollow dispensing assembly coupled to the walls of the shower enclosure, the dispensing assembly including an input adaptor to couple the water and chemical output line of the chemical dispensing member, the dispensing assembly also including a plurality of pin hole apertures.

* * * * *